United States Patent [19]

Chasar

[11] Patent Number: 4,590,017

[45] Date of Patent: May 20, 1986

[54] 2,4-BIS-(2,6-DI-T-ALKYL-4-SUBSTITUTED-PHENOXY)-1,3,2,4-DIOXADIPHOSPHETANES

[75] Inventor: Dwight W. Chasar, Northfield, Ohio

[73] Assignee: The B. F. Goodrich Company, Akron, Ohio

[21] Appl. No.: 703,063

[22] Filed: Feb. 19, 1985

[51] Int. Cl.$^4$ ............................................. C07F 9/146
[52] U.S. Cl. ...................................................... 558/73
[58] Field of Search .................................... 260/927 R

[56] References Cited

U.S. PATENT DOCUMENTS 4,507,416  3/1985  Chasar ............................ 260/927 R

*Primary Examiner*—Anton H. Sutto
*Attorney, Agent, or Firm*—J. Hughes Powell; Alan A. Csontos

[57] ABSTRACT

2,4-bis(2,6-di-t-alkyl-4-substituted-phenoxy)-1,3,2,4-dioxadiphosphetanes are prepared from 2,4,6-tris(substituted phenoxy)-1,3,5,2,4,6-trioxatriphosphorinanes.

9 Claims, No Drawings

2,4-BIS(2,6-DI-T-ALKYL-4-SUBSTITUTED-PHENOXY)-1,3,2,4-DIOXADIPHOSPHETANES

SUMMARY OF THE INVENTION 2,4-bis(2,6-di-t-alkyl-4-substituted-phenoxy)1,3,2,4-dioxadiphosphetanes are prepared from 2,4,6-tris(substituted phenoxy)-1,3,5,2,4,6-trioxatriphosphorinanes.

DETAILED DESCRIPTION

The novel 2,4-bis(2,6-di-t-alkyl-4-substituted-phenoxy)-1,3,2,4-dioxadiphosphetanes have the general formula

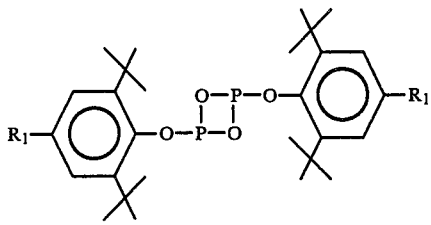

wherein + is t-butyl or t-pentyl and $R_1$ is hydrogen, primary, secondary and tertiary alkyl radicals containing 1 to 9 carbon atoms such as methyl, ethyl, isopropyl, n-butyl, t-butyl, amyl, t-amyl, hexyl, heptyl, 2-methyl hexyl, 2-ethyl hexyl, octyl, isooctyl, and the like; cycloalkyl radicals containing 3 to 6 carbon atoms; halogen; C≡N; alkoxy radicals containing 1 to 8 carbon atoms, such as methoxy, ethoxy, butoxy and the like; phenyl; $COOR_2$ wherein $R_1$ is an alkyl radical containing 1 to 8 carbon atoms; $—CH_2CH_2COOR_3$ wherein $R_3$ is an alkyl radical containing 1 to 18 carbon atoms; and $—C(CH_3)_2CON(R_4)_2$ wherein $R_4$ is an alkyl group containing 1 to 9 carbon atoms.

Preferably + is t-butyl and $R_1$ is hydrogen, an alkyl radical containing 1 to 4 carbon atoms, alkoxy radicals containing 1 to 4 carbon atoms, $—COOR_2$, $—CH(CH_3)_2CON(R_4)_2$ radicals wherein $R_2$ and $R_3$ are alkyl radicals containing 1 to 4 carbon atoms, and $R_4$ is an alkyl radical containing 1 to 4 carbon atoms.

Typical 2,4-bis(2,6-di-t-alkyl-4-substituted-phenoxy)-1,3,2,4-dioxadiphosphetanes include: 2,4-bis-(2,6-di-t-butyl-4-methylphenoxy)-1,3,2,4-dioxadiphosphetane; 2,4-bis(2,4,6-tri-t-butylphenoxy)-1,3,2,4-dioxadiphosphetane; 2,4-bis(2,6-di-t-butyl-4-ethylphenoxy)-1,3,2,4-dioxadiphosphetane; 2,4-bis(2,6-di-t-butyl-4-n-butylphenoxy)-1,3,2,4-dioxadiphosphetane; 2,4-bis(2,6-di-t-butyl-4-carbomethoxyphenoxy)-1,3,2,4-dioxadiphosphetane; 2,4-bis[2,6-di-t-butyl-4-(2-carboethoxyethyl)-phenoxy]-1,3,2,4-dioxadiphosphetane; 2,4-bis[2,6-di-t-butyl-4(1-methyl-1-diethylcarbamoylethyl-phenoxy]-1,3,2-4-dioxadiphosphetane; 2,4-bis(2,6-di-t-butyl-4-methoxyphenoxy)-1,3,2,4-dioxadiphosphetane; and the like.

The 2,4-bis(2,6-di-t-alkyl-4-substitued-phenoxy)-1,3,2,4-dioxadiphosphetanes are prepared by heating 2,4,6-tris(substituted phenoxy)-1,3,5,2,4,6-trioxatriphosphorinanes under vacuum at a temperature greater than about 100° C.

The 2,4,6-tris(substituted phenoxy)-1,3,5,2,4,6-trioxatriphosphorinanes may be represented by the structural formula

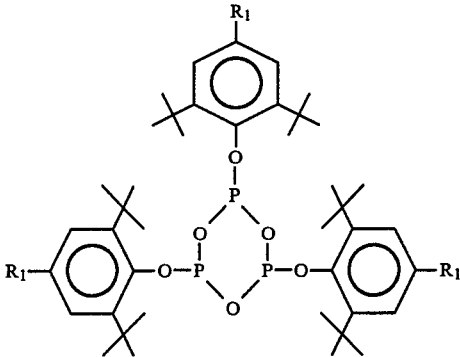

wherein + is t-butyl or t-pentyl and $R_1$ is hydrogen, primary, secondary, and tertiary alkyl radicals containing 1 to 9 carbon atoms such as methyl, ethyl, isopropyl, n-butyl, t-butyl, amyl, t-amyl, hexyl, heptyl, 2-methyl hexyl, 2-ethyl hexyl, octyl, isooctyl, and the like; cycloalkyl radicals containing 3 to 6 carbon atoms; halogen; C≡N; alkoxy radicals containing 1 to 8 carbon atoms, such as methoxy, ethoxy, butoxy and the like; phenyl; $COOR_2$ wherein $R_2$ is an alkyl radical containing 1 to 8 carbon atoms; $—CH_2CH_2COOR_3$ wherein $R_3$ is is an alkyl radical containing 1 to 18 carbon atoms; and $—C(CH_3)_2CON(R_4)_2$ wherein $R_4$ is an alkyl group of 1 to 9 carbon atoms.

Preferably + is t-butyl and $R_1$ is hydrogen, an alkyl radical containing 1 to 4 carbon atoms, alkoxy radicals containing 1 to 4 carbon atoms, $—COOR_2$, $—CH_2CH_2COOR_3$, and $—C(CH_3)_2CON(R_4)_2$ radical wherein $R_2$, $R_3$ and $R_3$ are alkyl radicals containing 1 to 4 carbon atoms.

Typical 2,4,6-tris(substituted phenoxy)-1,3,5,2,4,6-trioxatriphosphorinanes that may be used include 2,4,6-tris(2,6-di-t-butylphenoxy)-1,3,5,2,4,6-trioxatriphosphorinane and 2,4,6-tris(2,6-di-t-butyl-4-substuted phenoxy)-1,3,5,2,4,6-trioxatriphosphorinanes, wherein the radicals substituted at the 4-position are those described above. Typical compounds are 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6-di-t-butyl-4-n-butylphenoxy)-1,3,5,2,4,6-trioxatriphosphorinane, 2,4,6-tris(2,6-di-t-butyl-4-isoamylphenoxy)-1-3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5-2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6-tris[2,6-di-t-butyl-4-(1-methyl-1-di-ethylcarbamoylethyl)phenoxy]-1,3,5,2,4,6-trioxatriphosphorinane, and 2,4,6-tris[2,6-di-t-butyl-4-(2-carbooctadecyloxyethyl)phenoxy]-1,3,5,2,4,6-trioxatriphosphorinane.

The 2,4,6-tris(substituted phenoxy)-1,3,5,2-4,6-trioxatriphosphorinanes are readily prepared. A substituted phenylphosphorodichloridite is reacted with water and an amine in a non-protic solvent at low temperatures for short periods of time and the resulting 2,4,6-tris(substituted phenoxy)-1,3,5,2,4,6-trioxatriphosphorinane is obtained by filtering the reaction mixture, evaporating the filtrate and washing the crude product.

Substituted phenylphosphorodichloridites used include those substituted at the 2,6- and 2,4,6-positions on the phenyl group. The 2- and 6-positions are substituted with the t-butyl or t-pentyl groups, while the 4-position may be substituted with the alkyl, alkoxy, carboxyester, and like radicals as set forth for the

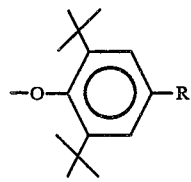

radical above.

Typical reactants include 2,6-di-t-butyl-4-methylphenylphosphorodichloridite, 2,6-di-t-butyl-4-ethylphenylphosphorodichloridite, 2,6-di-t-butyl-4-propylphenylphosphorodichloridite, 2,6-di-t-butyl-4-n-butylphenylphosphorodichloridite, 2,6-di-t-butyl-4-t-butylphenylphosphorodichloridite, 2,6-di-t-butyl-4-methoxyphenylphosphorodichloridite, 2,6-di-t-butyl-4-ethoxyphenylphosphorodichloridite, 2,6-di-t-butyl-4-carbomethoxyphenylphosphorodichloridite, 2,6-di-t-butylphenylphosphorodichlororidite, 2,6-di-t-butyl-4-(1-methyl-1-diethylcarbamoylethyl)phenylphosphorodichloridite and 2,6-di-t-butyl-4-(2-carboethoxyethyl)-phenylphosphorodichloridite and the like.

The amine used may be any amine, but more preferably is an alkylamine such as trialkylamines including trimethylamine, triethylamine, tripropylamine, wherein the alkyl radicals contain 1 to 8 carbon atoms, pyridine, N,N-dimethylaniline, and the like.

The solvents employed are organic non-protic solvents, that is, solvents free of groups such as hydroxyl represented by the alcohols. These solvents are characterized by at least partial solubility of the reactants in the solvent. Typical useful solvents include tetrahydrofuran, acetonitrile, chloroform, esters such as ethyl acetate, ethers such as dioxane, and even hydrocarbon solvents such as toluene and the like.

The molar ratios of the reactants normally used are about one mol of the substituted phenylphosphorodichloridite, one mol of water and two mols of the amine. While these proportions may be varied within a range of about 1 to 0.8–2.0 to 0.5–10, better yields are obtained when the 1:1:2 mol ratio is generally observed. Of course, an excess of any reactant may be used but the yield will depend on there being at least one mol of water and one mole of amine present.

The reaction is quite rapid and usually is conducted at about 0° C. to control the reaction rate, although the reaction temperature may vary from about −10° C. to 25° C. The reaction products prepared in accordance with this process normally need only be filtered as the reaction product is dissolved in the solvent, the solvent is evaporated and the resulting dry product washed, as with a mild aqueous alkaline solution, then washed with water and dried.

Typical preparations of 2,4,6-tris(substituted phenoxy)-1,3,5,2,4,6-trioxatriphosphorinanes are found in Examples I and II.

EXAMPLE I 2,4,6-tris(2,4,6-tri-t-butylphenoxy)-1,3,5,2,4,6-trioxatriphosphorinane 6.0 grams (0.017 mol) of 2,4,6-tri-t-butylphenylphosphorodichloridite and 3.34 grams (0.033 mol) of triethylamine were dissolved in 100 ml of tetrahydrofuran, and the solution was cooled to 0°–5° C. 0.30 gram (0.017 mol) of water was added to the solution and the mixture was stirred for 0.5 hour. The resulting reaction mixture was filtered and the filtrate was evaporated to a dry white glass. The glassy product was stirred three times with saturated aqueous sodium bicarbonate solution for ten minutes, each was then filtered, washed with water and air dried to provide the white solid product in about 70% yield. Two recrystallizations from ethyl acetate gave crystals, mp 226°–244° C., density 1.14.

EXAMPLE II 2,4,6-tris(2,6-di-t-butyl-4-methylphenoxy)-1,3,5,2,4,6-trioxatriphosphorinane 6.0 grams (0.019 mol) of 2,6-di-t-butyl-4-methylphenylphosphorodichloridite and 3.78 grams (0.037 mol) of triethylamine were dissolved in 100 ml of tetrahydrofuran, and the solution was cooled to 0°–5° C. 0.34 gram (0.019 mol) of water was added to the solution and the mixture was stirred for 0.5 hour. The resulting reaction mixture was filtered and the filtrate was evaporated to a dry white glass. The dry product was stirred twice with saturated aqueous sodium bicarbonate solution for ten minutes, filtered, washed with water and air dried to provide the white solid (4.04 grams). After washing in methanol, the solid had a mp 170°–184° C.

To prepare the novel 2,4-bis(2,6-di-t-alkyl-4-substituted-phenoxy)-1,3,2,4-dioxadiphosphetanes, the defined 2,4,6-tris(substituted phenoxy)-1,3,5,2,4,6-trioxatriphosphorinanes are heated at a temperature between about 100° C. to about 300° C., depending on the melting point or boiling point of the 2,4,6-tris(substituted phenoxy)-1,3,5,2,4,6-trioxatriphosphorinanes. When these are solids at below 100° C., the temperature used is a temperature just above the melting point so long as it is at least about 100° C. The reactions proceed under vacuum of between 0.1 mm to about 50 mm, preferably between about 1 and 10 mm. The reactions are readily conducted in a sublimation or by means of a flash vacuum pyrolysis set up. The reaction product, the 2,4-bis(2,6-di-t-alkyl-4-substituted-phenoxy)-1,3,2,4-dioxadiphosphetane, are collected by condensation, washing and recrystallized from a solvent.

Typical preparations are described in Examples III and IV.

The structures of the 2,4-bis(2,6-di-t-alkyl-4-substituted-phenoxy)-1,3,2,4-dioxadiphosphetanes were confirmed by infrared and nuclear magnetic resonance spectra. Molecular weights were determined and confirmed by field desorption mass spectra (FD/MS) and fast atom bombardment mass spectra (FAB/MS) or Vapor Phase Osmometry (VPO).

EXAMPLE III 2,4-bis(2,6-di-t-butyl-4-methylphenoxy)1,3,2,4-dioxadiphosphetane 10 grams of purified 2,4,6-tris(2,6-di-t-butyl-4-methylphenoxy)-1,3,5,2,4,6-trioxatriphosphorinane was placed in a large sublimation apparatus with a water cooled cold finger. The sublimator was heated in an oil bath at 220° C. and 8 mm vacuum for about 6 hours. During this time, a white solid product collected on the cold finger. This material was scraped off to yield about 7 grams of crude product. The crude product was stirred in a minimal amount of ethyl ether for purification. 5 grams (50% yield) of nearly pure product was obtained. This solid may be recrystallized from chloroform. The melting point was 174°–182° C.; Infrared spectrum (in Nujol): strong absorptions at 1095 cm$^{-1}$ (Ar—O), 890 cm$^{-1}$ (P—O—P), 772 and 755 cm$^{-1}$; Proton NMR spectrum (in deuteriochloroform): 1.48 ppm (t-butyl), 2.30 ppm (methyl) and 7.14 ppm (Ar—H), all singlets downfield from internal (CH$_3$)$_4$Si; $^{31}$P NMR spectrum (in chloroform) 176.5 ppm, downfield from external phosphoric acid; Field Desorption/Mass Spectrum: m/e is 532; Vapor Phase Osmometry (45° in chloroform) is 548; the theoretical molecular weight is 532.

EXAMPLE IV

2,4-bis(2,4,6-tri-t-butylphenoxy)-1,3,2,4-dioxadiphosphetane 10 grams of purified 2,4,6-tri-t-butylphenoxy)-1,3,5,2,4,6-trioxatriphosphorinane was placed in the sublimator apparatus with a water cooled cold finger. The sublimator was heated in an oil bath at 250° C. and 9 mm vacuum for about 6 hours. During this time, a white solid product collected on the cold finger. This material was scraped off to yield about 6.5 grams of crude product. The crude product was stirred in a minimal amount of ethyl ether for purification. 4.5 grams (45% yield) of nearly pure product was obtained. The melting point was 196° to 218° C.; Infrared spectrum (in Nujol): 1095 cm$^{-1}$ (Ar—O), 890 to 875 cm$^{-1}$ (P—O—P); Proton NMR spectrum (in deuteriochloroform): 1.31 ppm (p-t-butyl), 1.50 ppm (o-t-butyls) and 7.36 ppm (Ar—H), all singlets downfield from internal (CH$_3$)$_4$Si; Field Desorption/Mass Spectrum: m/e is 616; the theoretical molecular weight is 616.

The 2,4-bis(2,6-di-t-alkyl-4-substituted-phenoxy)-1,3,2,4-dioxadiphosphetanes of this invention are novel and unique organic phosphorous compounds, with an unusual and unexpected degree of activity. They decompose peroxides almost instantaneously, even at room temperature, in contrast to typical organic phosphites that require several hours to decompose hydroperoxides. The novel materials may be used as stabilizers, and as antioxidants for a variety of organic materials subject to attack by oxygen, for example: polymers, oils and the like. They may be used in combination with known antioxidants to enhance the stabilizing activity of other stabilizers, especially when used in combination with hindered phenols as in polyolefins, for example. They may also be used as a stabilizer for ethers.

I claim:

1. 2,4-bis(2,6-di-t-alkyl-4-substituted-phenoxy)-1,3,2,4-dioxadiphosphetanes having the structure

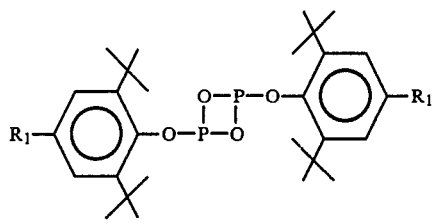

wherein + is t-butyl or t-pentyl and R$_1$ is hydrogen, primary, secondary, and tertiary alkyl radicals containing 1 to 9 carbon atoms such as methyl, ethyl, isopropyl, n-butyl, t-butyl, amyl, t-amyl, hexyl, heptyl, 2-methyl hexyl, 2-ethyl hexyl, octyl, isooctyl, and the like; cycloalkyl radicals containing 3 to 6 carbon atoms; halogen; C≡N; alkoxy radicals containing 1 to 8 carbon atoms, such as methoxy, ethoxy, butoxy and the like; phenyl; COOR$_2$ wherein R$_2$ is an alkyl radical containing 1 to 8 carbon atoms; —CH$_2$CH$_2$COOR$_3$ wherein R$_3$ is is an alkyl radical containing 1 to 18 carbon atoms, and —C(CH$_3$)$_2$CON(R$_4$)$_2$ wherein R$_4$ is an alkyl group of 1 to 9 carbon atoms.

2. 2,4-bis(2,6-di-t-alkyl-4-substituted-phenoxy)-1,3,2,4-dioxadiphosphetanes of claim 1 wherein + is t-butyl and R$_1$ is hydrogen, an alkyl radical containing 1 to 4 carbon atoms, alkoxy radicals containing 1 to 4 carbon atoms, —COOR$_2$, —CH$_2$CH$_2$COOR$_3$ and —C(CH$_3$)$_2$CON(R$_4$)$_2$ radicals wherein R$_2$, R$_3$ and R$_4$ are alkyl radicals containing 1 to 4 carbon atoms.

3. A 2,4-bis(2,6-di-t-alkyl-4-substituted-phenoxy)-1,3,2,4-dioxadiphosphetane of claim 2, 2,4-bis(2,6-di-t-butyl-4-methylphenoxy)-1,3,2,4-dioxadiphosphetane.

4. A 2,4-bis(2,6-di-t-alkyl-4-substituted-phenoxy)-1,3,2,4-dioxadiphosphetane of claim 2, 2,4-bis(2,4,6-tri-t-butylphenoxy)-1,3,2,4-dioxadiphosphetane.

5. A 2,4-bis(2,6-di-t-alkyl-4-substituted-phenoxy)-1,3,2,4-dioxadiphosphetane of claim 2, 2,4-bis(2,6-di-t-butyl-4-ethylphenoxy)1,3,2,4-dioxadiphosphetane.

6. A 2,4-bis(2,6-di-t-alkyl-4-substituted-phenoxy)-1,3,2,4-dioxadiphosphetane of claim 2, 2,4-bis(2,6-di-t-butyl-4-n-butylphenoxy)-1,3,2,4-dioxadiphosphetane.

7. A 2,4-bis(2,6-di-t-alkyl-4-substituted-phenoxy)-1,3,2,4-dioxadiphosphetane of claim 2, 2,4-bis(2,6-di-t-butyl-4-carbomethoxyphenoxy)-1,3,2,4-dioxadiphosphetane.

8. A 2,4-bis(2,6-di-t-alkyl-4-substituted-phenoxy)-1,3,2,4-dioxadiphosphetane of claim 2, 2,4-bis[2,6-di-t-butyl-4-(2-carboethoxyethyl)-phenoxy]-1,3,2-4-dioxadiphosphetane.

9. A 2,4-bis(2,6-di-t-alkyl-4-substituted-phenoxy)-1,3,2,4-dioxadiphosphetane of claim 2, 2,4-bis[2,6-di-t-butyl-4-(1-methyl-1-diethylcarbamoylethyl-phenoxy]-1,3,2,4-dioxadiphosphetane.

* * * * *